(12) United States Patent
Slater et al.

(10) Patent No.: US 10,228,314 B2
(45) Date of Patent: Mar. 12, 2019

(54) GAS SENSOR

(71) Applicant: ECOLE POLYTECHNIQUE FEDERALE DE LAUSANNE (EPFL), Lausanne (CH)

(72) Inventors: Conor Slater, Murten (CH); Gaël Farine, Lausanne (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 85 days.

(21) Appl. No.: 15/508,247

(22) PCT Filed: Sep. 1, 2015

(86) PCT No.: PCT/EP2015/069897
§ 371 (c)(1),
(2) Date: Mar. 2, 2017

(87) PCT Pub. No.: WO2016/034558
PCT Pub. Date: Mar. 10, 2016

(65) Prior Publication Data
US 2017/0284919 A1    Oct. 5, 2017

(30) Foreign Application Priority Data
Sep. 2, 2014    (EP) .................................... 14183247

(51) Int. Cl.
*G01N 11/08*    (2006.01)
*G01N 33/22*    (2006.01)

(52) U.S. Cl.
CPC ........... *G01N 11/08* (2013.01); *G01N 33/225* (2013.01)

(58) Field of Classification Search
CPC .................................................... G01N 11/08
See application file for complete search history.

(56) References Cited

U.S. PATENT DOCUMENTS

| | | |
|---|---|---|
| 5,311,447 A | 5/1994 | Bonne |
| 2009/0229351 A1 | 9/2009 | Ryser |

OTHER PUBLICATIONS

International Search Report and Written Opinion issued by the International Searching Authority, dated Sep. 28, 2015, in related International Patent Application No. PCT/EP2015/069897; 9 pages.

*Primary Examiner* — Paul M. West
(74) *Attorney, Agent, or Firm* — Faegre Baker Daniels LLP (57) ABSTRACT

Gas sensor (2) for measuring properties of a gas (1), including a gas viscosity sensor (4) comprising a gas interface portion (20) in contact with the gas (1) to be measured, and a measuring chamber system (15) comprising a measuring chamber (16), a first resistive passage (18) fluidically connecting the measuring chamber (16) to the gas interface portion (20), a pressure generator (25) configured to generate a change in pressure in the measuring chamber, and a pressure sensor (28) configured to measure a time dependent variation in pressure of gas in the measuring chamber, the time dependent variation of pressure in the measuring chamber due to flow of gas through the resistive passage being correlated to a viscosity of the gas. The gas viscosity sensor further comprises a reference chamber system (21) comprising a reference chamber and a second resistive passage (24) fluidically interconnecting the reference chamber (22) to the gas interface portion (20), the reference chamber (22) being coupled to the pressure sensor (28) of the measuring chamber such that the pressure sensor is configured to measure a differential pressure between a pressure in the measuring chamber and a pressure in the reference chamber.

23 Claims, 9 Drawing Sheets

GAS SENSOR

This application claims priority to PCT application number PCT/EP2015/069897 filed Sep. 1, 2015, which in turn claims priority from EP Patent application number EP 14183247.7 filed Sep. 2, 2014, the subject matter of which are incorporated herein by reference.

The present invention relates to sensor for determining the properties of a gas, in particular a combustible gas in order to optimize the combustion thereof.

There are many applications in which it is useful to determine the parameters of a gas, such as measured by the present invention. In particular, in the case of natural gas, it is especially useful to know some properties of natural gas in order to optimize the combustion and operate the burner or engine in a safe way, to monitor the production or blending of natural gas or biogas, or to monitor the energy delivered throughout the natural gas supply chain, amongst other applications.

Natural gas comes from a variety of sources and is mixed by networks operators a number of times before reaching its point of use. This means that the composition of natural gas can vary significantly and this has an impact on air requirements to ensure an optimal combustion. The optimum air (oxygen) needed to ensure an optimal combustion in a system changes as the composition of natural gas varies and two parameters of interest of the lambda value $\lambda$ and the Wobbe index ($W_o$).

The Wobbe index can be determined by measuring the gas viscosity, as explained in more details here below. However, the relation between the gas viscosity and the Wobbe index is not perfect, and that is why the measurement of the gas viscosity can be corrected by using the measurement of the thermal-conductivity of the same gas or the measurement of carbon dioxyde content, as described here below.

The stoichiometric air requirement of a fuel is the amount of dry air required to completely combust one mole of fuel gas (with air only 20.9% oxygen). The air/fuel (A/F) ratio for every mole of a hydrocarbon fuel $C_xH_y$ to achieve complete combustion is defined by $$(A/F)_{stoich} = 4.785\left(x + \frac{1}{4}y\right)$$

Table 1 below shows selected hydrocarbons and their corresponding air requirements

TABLE 1

AIR TO FUEL RATIO REQUIREMENTS FOR
THE COMBUSTION OF SELECTED ALKANES

| component i | $(A/F)_{stoich}$ |
|---|---|
| methane | 9.57 |
| gasoline | 14.7 |
| ethane | 16.75 |
| propane | 23.93 |
| butane | 31.1 |
| pentane | 38.28 |

For a mixture of gases with the composition [Xi] the air to fuel ratio can be calculated from $$(A/F)_{stoich} = \sum_i (A/F)_{stoich,i}$$

The lambda value $\lambda$ is defined by $$\lambda = \frac{(A/F)_{actual}}{(A/F)_{stoich}}$$

In combustion the fuel and the volume of air flow, V' depends on the density $\rho$ by the relation $$V' = C\sqrt{\frac{2\nabla p}{\rho}}$$

where $\nabla p$ is the pressure drop across the inlet orifice and C is some constant. Because of the dependence on the density one has to introduce the combustion air requirement index CARI by the definition $$CARI = (A/F)_{stoich}\sqrt{\frac{\rho_{air}}{\rho_{fuel}}}$$

If the CARI is known one can adjust the air flow to obtain the required value for $\lambda$. The Wobbe index $W_o$ determines the required air flow and is defined as $$W = H_0\sqrt{\frac{\rho_{air}}{\rho_{fuel}}}$$

where $H_0$ is the caloric value

It turns out that for the range of composition in natural gas one finds that the Wobbe index and CARI are related via $$W = 97.732 CARI - 29.692$$

For various reasons the requirement to obtain the correct value for $\lambda$ is usually discussed in the literature via the Wobbe index and not the CARI. The Wobbe index is an important criterion of inter-changeability of gases for industrial applications. Gas composition variation does not change the air requirement and velocity burning when the Wobbe index remains almost constant. However, the relationship between the Wobbe index and viscosity is not perfect.

The choice of the correct value of $\lambda$ also depends on the application. In a natural gas appliance or engine, the quality of the fuel is subject to changes, and therefore it is useful to know the Wobbe index in order to control the combustion. The Wobbe index can be measured before, during and after the combustion. Methods to measure during the combustion are based on the ionization current of the flame emission and/or the temperature probing. Post-combustion methods use oxygen sensor (excess air ratio) to determine the air/fuel ratio of the combustion. The drawbacks of those methods are that they are complex and costly. Also, reliability is an issue as they are located in the combustion chamber or in the exhaust of the combustion, and make them prone to drift. Furthermore, none of those methods are helpful for ignition applications. Having a sensor installed in the inlet allows changing air/fuel ratio before the start of an appliance thus avoiding ignition problems.

An object of the invention is to provide a sensor that enables the accurate measurement of the viscosity of a gas, while being compact and economical to produce and assemble.

A more specific object of the invention, for applications related to combustible gases, in particular natural gas, is to provide a sensor that enables the accurate measurement of the Wobbe index of a gas, while being compact and economical to produce and assemble.

It is advantageous to provide a gas sensor that is reliable, easy to implement and economical to use.

It is advantageous to provide a gas sensor that is robust and stable over its intended lifetime.

As shown in the publication "Natural gas: physical properties and combustion features", Bonne et al. (2006) proposed the following general equation $$H_0 = 3643.53 + 1050.71\left(\frac{102}{\eta}\right)^3 - 7.60221\lambda_{T_H} - 2294.2\left(\frac{\lambda_{T_L}}{\lambda_{T_H}}\right)$$

where $\lambda$ is the thermal conductivity (cal/s m° C.) and $T_L$, $T_H$ are the low and high temperatures respectively (° C.), $\eta$ is the gas viscosity (µpoise).

By measuring the thermal conductivity of the gas at two temperatures, the higher heating value (HHV) can be determined and the accuracy of the Wobbe Index measurement can be improved.

Furthermore, a carbon dioxide sensor can also be used to improve the accuracy of the Wobbe index measurement.

A gas sensor according to embodiments of the invention is configured to measure the viscosity of a gas, and one or more additional parameters selected from a group including the thermal-conductivity, the carbon dioxide content, temperature, pressure, humidity, and the Wobbe index of a gas. The additional parameters are useful to obtain the correct value for $\lambda$.

They are a number of application cases where a system could benefit from a Wobbe index sensor that is reliable, robust, compact, cost-effective and that can operate in the inlet of a natural gas appliance or engine, or for natural gas production, blending or distribution. A non-exhaustive list of examples include: boilers, furnaces, water heaters, co-generation engines, turbines, micro turbines, fuel cells.

Natural gas appliances and engines with adjustable air/fuel ratio can benefit from a Wobbe index sensor according to embodiments of the invention. The sensor may be integrated into the natural gas inlet of the appliance or engine and ensures that the combustion remains efficient. As the composition of natural gas changes, the optimum air requirements for the appliance or engine can be adjusted based on the Wobbe index measured in the inlet of the appliance or engine. Also, ignition problems are reduced as the Wobbe index is measured even before the appliance is started, and the appliance or engine can start with the right optimum air requirements. The Wobbe index sensor is reliable as it does not react with the gas, is robust and does not have any moving parts, compact and cost-effective, allowing it to be integrated in a variety of natural gas appliances or engines.

Regarding applications in natural gas vehicles (trucks, cars, motorbikes, boats, planes), there are strong variations in the composition of natural gas fuel for vehicles depending on the location of the gas station and also important seasonal changes in the composition between winter and summer. This makes that the mixing effects of different fuel compositions inside the tank of a natural gas vehicle are hard to predict. To overcome ignition and combustion problems tied to the variation of fuel composition, a Wobbe index sensor according to the invention can be integrated to measure parameters of the fuel of a natural gas vehicle. The air/fuel ratio of the composition can therefore be adjusted to an optimum, before the ignition or during the combustion.

Regarding applications in biogas production and gas flare, aerobic, anaerobic and hybrid bioreactors produce biogas due to the fermentation of a variety of biodegradable materials. Monitoring of the methane content of the gas produced is essential to control the feedstock rate and ensure the stability of the reaction. One important parameter for the control of the biodigestion reaction is to measure the methane content of the biogas produced. As the methane content can be correlated to Wobbe Index, a gas sensor according to embodiments of the invention can be applied to biogas production monitoring. The rate the feedstock is fed into a biodigestor can be controlled by the output measurement of the Wobbe index of the biogas produced. Also, the present sensor can measure the Wobbe Index of the gas flowing in a flaring outlet, and based on this information the gas is flared or released.

Regarding applications in natural gas distribution, or integration into gas meter, a gas sensor according to embodiments of the invention can be integrated together with a gas flow meter. Such a system can provide data on the volume and energy content delivered at a certain point of the natural gas grid.

For portable applications, a gas sensor according to embodiments of the invention is compact and low-power enough to be integrated into a portable Wobbe index meter. Such a handheld instrument may run on batteries and may be connected to a natural gas line to measure the Wobbe index of the gas.

The present invention can also be simply used for the measurement of the gas viscosity, where it is needed.

Disclosed herein is a sensor for measuring properties of a gas, including a gas viscosity sensor comprising a gas interface portion in contact with the gas to be measured, and a measuring chamber system comprising a measuring chamber, a first resistive passage fluidically connecting the measuring chamber to the gas interface portion, a pressure generator configured to generate a change in pressure in the measuring chamber, and a pressure sensor configured to measure a time dependent variation in pressure of gas in the measuring chamber, the time dependent variation of pressure in the measuring chamber due to flow of gas through the resistive passage being correlated to a viscosity of the gas. The gas viscosity sensor further comprises a reference chamber system comprising a reference chamber and a second resistive passage fluidically interconnecting the reference chamber to the gas interface portion, the reference chamber being coupled to the pressure sensor of the measuring chamber such that the pressure sensor is configured to measure a differential pressure between a pressure in the measuring chamber and a pressure in the reference chamber.

In an advantageous embodiment, the first resistive passage and second resistive passage are in the form of capillary channels.

In an advantageous embodiment, the pressure sensor comprises an elastically deformable membrane the displacement of which provides a measurement value of the differential pressure, the deformable membrane forming an interface between a volume of gas contained in the measuring chamber and the volume of gas contained in the reference chamber.

In an advantageous embodiment, the pressure generator of the measuring chamber system comprises a heater positioned in the measuring chamber and configured to heat the gas therein, and a heat evacuator to cool the gas in the measuring chamber.

In an advantageous embodiment, the heat evacuator is in the form of a heat sink formed of a mass of thermally conductive material with a heat capacity significantly larger than the heat capacity of the gas contained in the measuring chamber.

In an advantageous embodiment, the heat sink is made of a block of metal with a thermal diffusivity greater than $8 \times 10^{-5}$ m²/s.

In an advantageous embodiment, the gas sensor further comprises a signal processing circuit comprising a circuit board.

In an advantageous embodiment, the measuring chamber is formed in a cavity provided in a heat sink of the measuring chamber system.

In an advantageous embodiment, the pressure generator comprises a heater, the heater comprising a resistive element formed as resistive circuit traces on the circuit board, or as a resistance element mounted directly on the circuit board.

In an advantageous embodiment, the reference chamber is arranged on an opposite side of the circuit board to the measuring chamber.

In an advantageous embodiment, the pressure sensor is mounted within the reference chamber and fluidically connected via an orifice in the circuit board to the measuring chamber.

In an advantageous embodiment, the gas interface portion comprises a housing defining a gas receiving chamber connected via an inlet and outlet to a gas flow system through which the gas to be measured flows.

In an advantageous embodiment, the sensor may further comprise one or more auxiliary sensors selected from a group comprising $CO_2$ sensor, humidity sensor, temperature sensor, thermal conductivity sensor, absolute pressure sensor.

In an advantageous embodiment, the auxiliary sensor includes at least a $CO_2$ sensor.

In an advantageous embodiment, at least some of the auxiliary sensors are positioned in a gas receiving chamber of the gas interface portion.

In an advantageous embodiment, at least some of the auxiliary sensors are mounted on the circuit board.

Further objects and advantageous features of the invention will be apparent from the claims, from the detailed description, and annexed drawings, in which:

FIGS. 2a, 3a and 4a are perspective partial cross sectional views of a gas sensor according to an embodiment of this invention, and FIGS. 2b, 3b and 4b are detailed views of respective portions of FIGS. 2a, 3a and 4a;

FIG. 4a is another perspective partial cross sectional view of the gas sensor of FIG. 2a, and FIG. 4b is a detailed view of a portion of FIG. 4a;

Referring to the figures, starting mainly with FIGS. 1 and 2a to 4b, a gas sensor 2 according to an embodiment of this invention is configured for measuring the viscosity of a gas 1 and may be further configured to measure other properties of the gas including for instance the temperature, the humidity, the thermal conductivity, the proportion of certain gas components in particular $CO_2$ (carbon dioxide) and the absolute pressure thereof. The measurement of the viscosity of the gas and other parameters mentioned in the aforegoing is particularly useful in the determination of the Wobbe index of the gas in order to optimize combustion thereof. As discussed above in the introduction, natural gas may comprise various combustible components such that the amount of oxygen or air required to obtain stoichiometric combustion varies as a function of the composition of the gas but also of its temperature and pressure. It may be noted however that within the scope of the invention the viscosity determination as well as the determination of other parameters such as pressure, temperature, humidity, $CO_2$ content, absolute pressure in a gas sensor may be used for other applications not related to the determination of the Wobbe index, for instance to assess the purity of gas compositions, e.g. when forming a gas mixture of $N_2$ and $H_2$.

Figure 1:
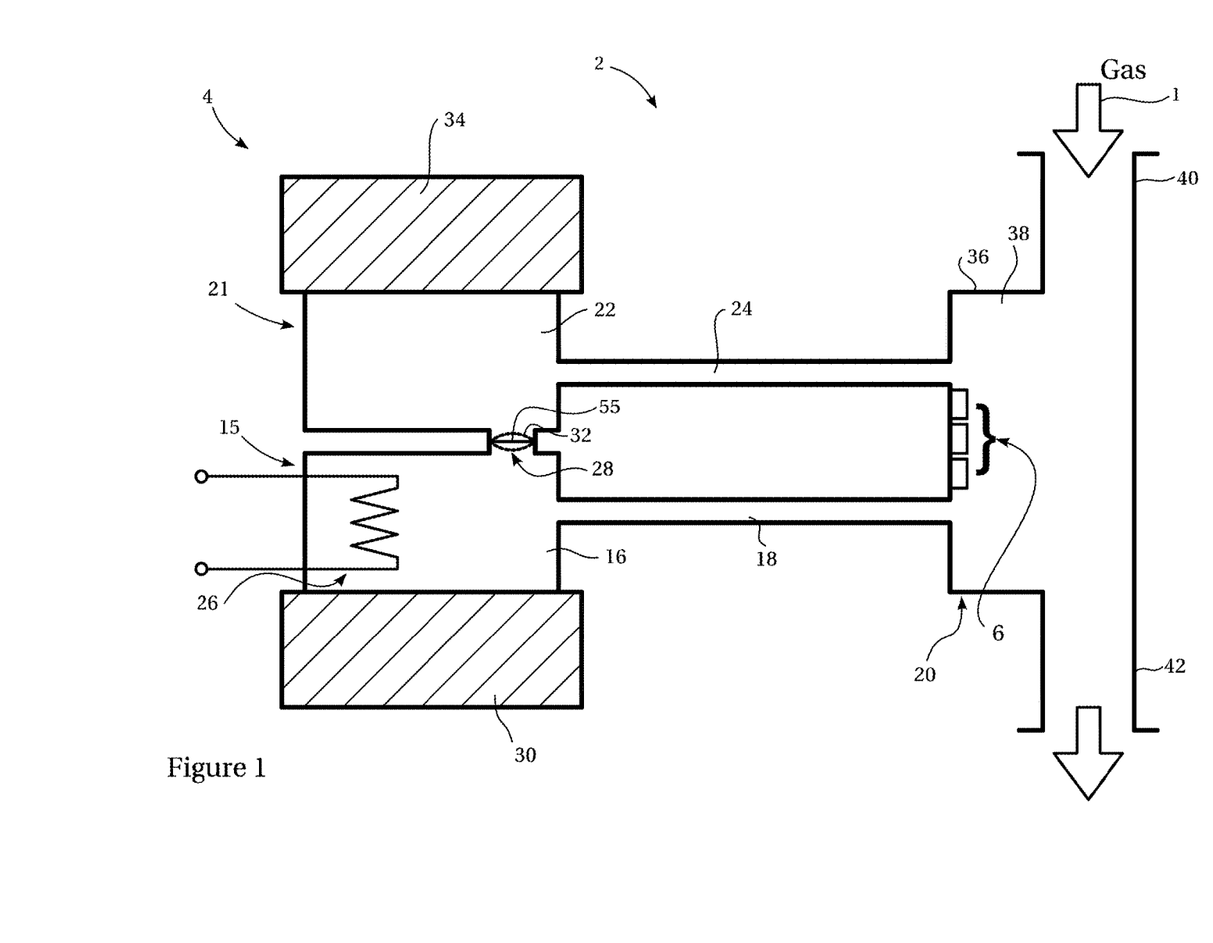
FIG. 1 is a schematic representation of a gas sensor according to an embodiment of the invention.
Figure 2A:
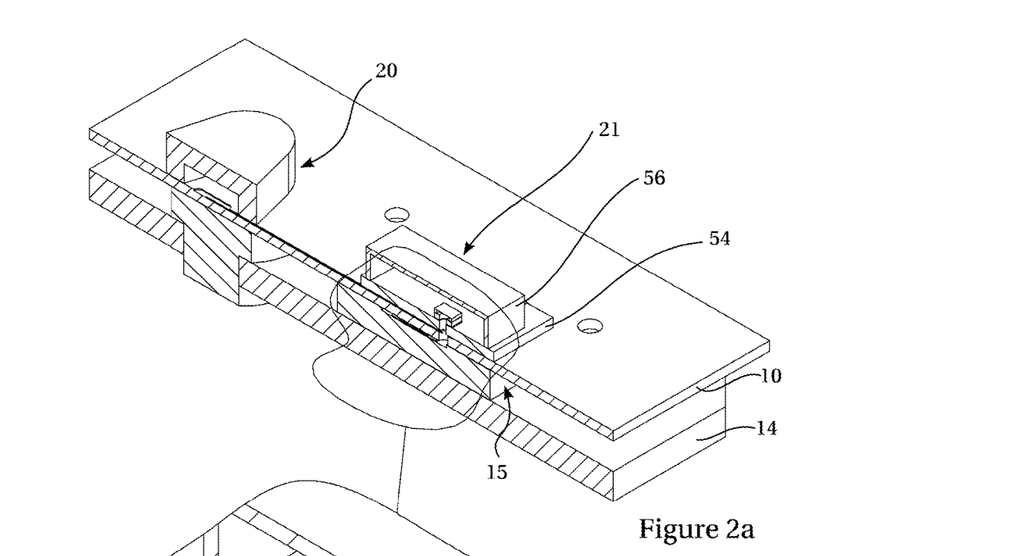
Figure 2B:
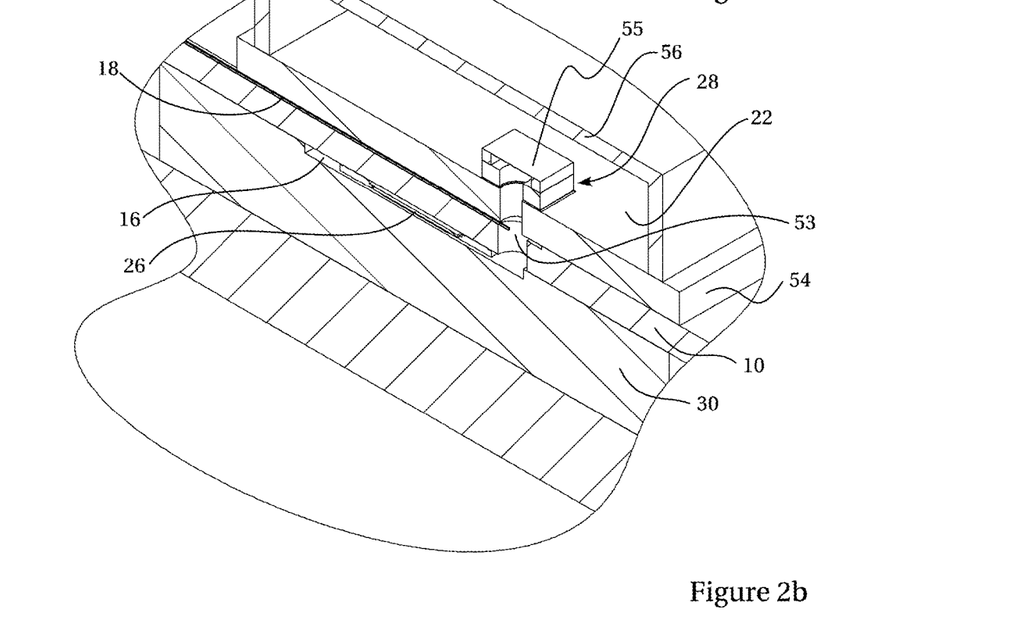
Figures 3A, 3B:
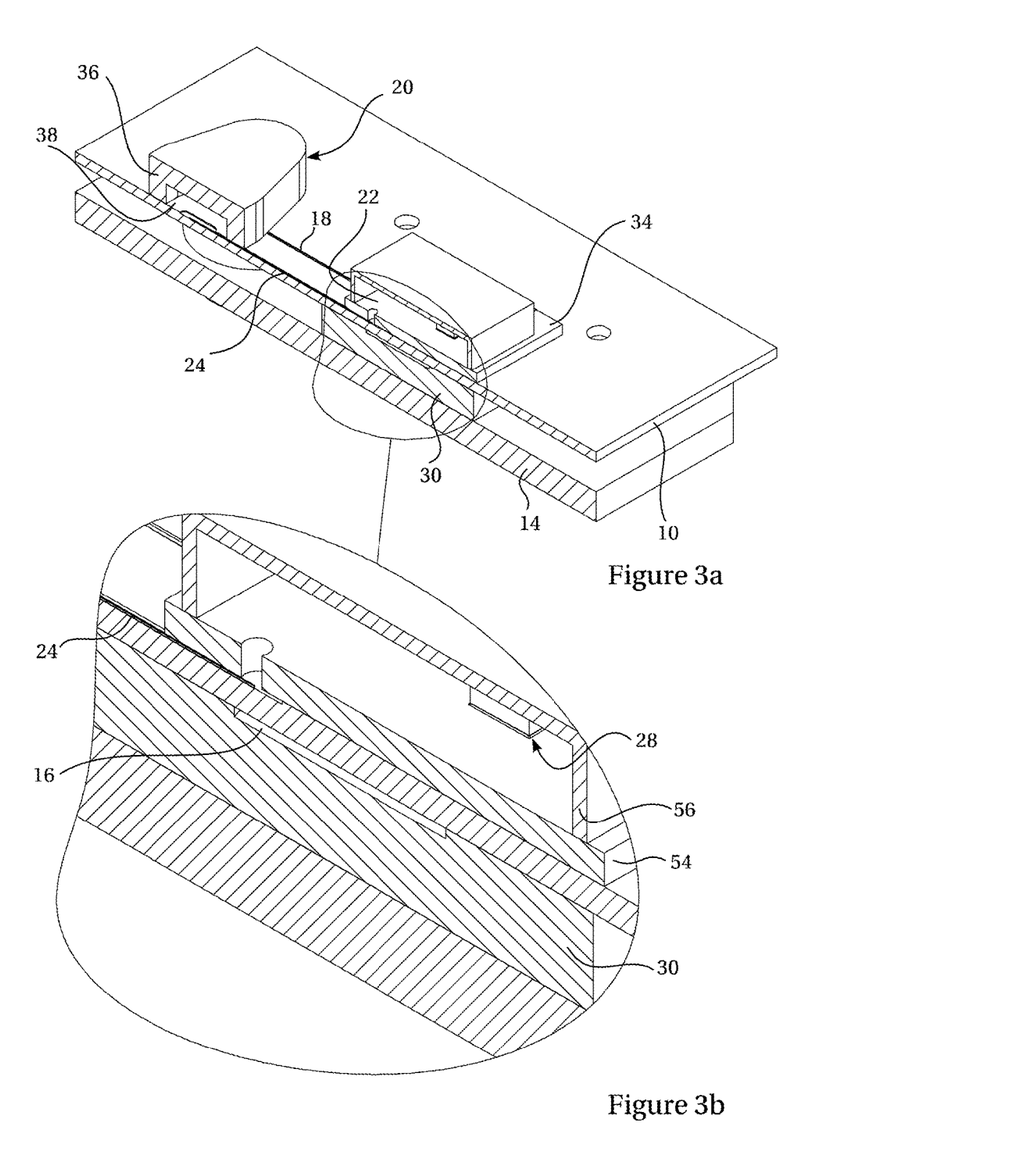

According to an embodiment of the invention, the gas sensor 2 comprises a gas viscosity sensor 4, auxiliary sensors 6, and a signal processing circuit 8 configured to electronically control the operation of the sensor and to process of the measured signals in order to output a measurement value or values relating to the measured properties of the gas 1. Measurement values may include any one or more of viscosity, humidity, temperature, pressure, thermal conductivity, and other measured values, or a composite measurement value, such as a Wobbe index value, resulting from a computation of, or correlation with, various basic measurement values. The outputted measurement value or values may be used by an external control system to control for instance the combustion process of a combustible gas in a heat producing device or in an engine or any device based on combustion of gas.

The gas sensor 4 may form a single unit mounted in a common housing or on a common support structure 14, but within the scope of the invention it is also possible to have a plurality of structurally independent and separable sensors or components. For instance, the gas viscosity sensor and the auxiliary sensors could be separate components although in a preferred embodiment the various sensors are integrated into a single unit for a compact and cost effective arrangement. The signal processing circuit 8 may comprise a circuit board 10 and one or more micro-processors or micro-controllers 12 mounted on the circuit board and electrically interconnected to sensors such as the gas viscosity sensor 4 and the auxiliary sensors 6.

The auxiliary sensors 6 may advantageously comprise a carbon dioxide sensor 44, a humidity sensor 46, a temperature sensor 48, a thermal conductivity sensor 50 and an absolute pressure sensor 52. These auxiliary sensors may advantageously be mounted in a housing 36 of a gas interface portion 20 comprising an inlet 40 and an outlet 42 communicating with a gas receiving chamber 48 in which the auxiliary sensors may be mounted. As mentioned above, it is also possible to mount some or all of the auxiliary sensors in other units or in other sections of the gas sensor.

The gas 1 to be measured flows into the gas receiving chamber 38 through the inlet 40 and out through the outlet 42, the auxiliary sensors 6 being in contact with the gas to be measured.

The gas viscosity sensor 4 comprises a measuring chamber system 15 comprising a measuring chamber 16 fluidically interconnected to the gas receiving chamber 38 through at least one resistive passage 18, the measuring chamber 16 further comprising a pressure generator 25 and a pressure sensor 28. The resistive passage forms a fluidic resistance which restricts the flow of gas into and out of the measuring chamber. The measuring chamber encloses a volume of gas where the pressure can be varied either positively or negatively with respect to the gas interface portion.

The pressure generator in a preferred embodiment comprises a heater 26 and a heat evacuator 30.

The heater is a component which can transfer heat to the gas in the cavity to cause an increase in pressure. The heater may be of various types such as a resistive heater, an ultrasonic emitters, microwave emitter, infrared lamp, or induction heater. In an advantageous embodiment, the heater may comprise a thin membrane with a resistive conducting area that is held approximately in the centre of the measuring chamber, by a supporting structure. The heater is configured to have a low heat capacity relative to the heat evacuator to sure rapid cooling of the gas when the heater is switched off.

Figure 8:
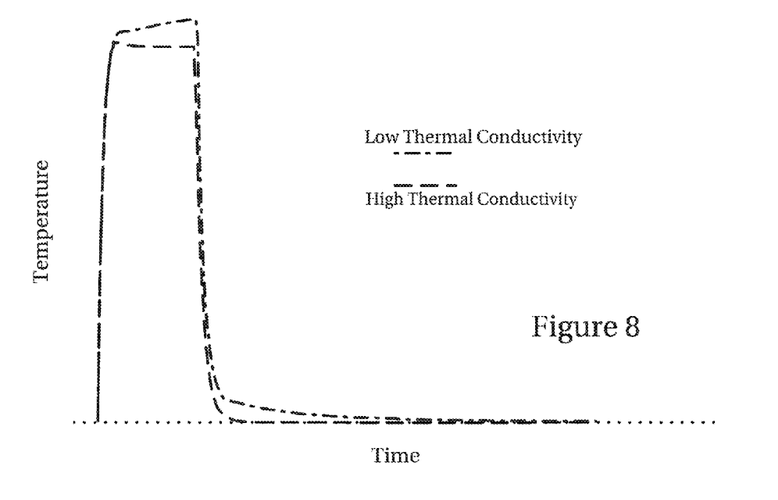
FIG. 8 is a graphical representation of a temperature vs time behavior of a measuring chamber of a gas sensor according to an embodiment of the invention.

The heat evacuator 30 may be in the form of a passive heat sink made of a thermally highly conductive material with a high heat capacity relative to the heat capacity of the gas contained in the measuring chamber 16. The heat evacuator may be cooled by natural convection or may be actively cooled by a fluidic cooling system although in a preferred embodiment a passively cooled heat sink constituted for example by a relatively large block of metal provides sufficiently effective cooling effect for purposes of determining the viscosity of a gas according to the present invention. To improve the precision of the sensor it is important to have a high rate of heat conduction between the gas in the measuring chamber and the heater, respectively the heat evacuator. FIG. 8 shows the decay in temperature of the gas within the measuring chamber from the moment when the heater is switched off, for two heatsink materials of different thermal conductivities. A longer temperature decay will have more of an effect on the time constant of the pressure normalising within the measuring chamber, thus if the absolute temperature is not controlled from measurement to measurement there will be variation in the time constant of the pressure increase. As precisely controlling the temperature of the gas in the cavity would be difficult, maximising the heat transfer between the gas and the measuring chamber heat evacuator increases the precision of the sensor.

In a preferred embodiment, the measuring chamber 16 is formed at least partially as a cavity within a heatsink 30, which may be constructed from any material which can hold the gas and conduct heat away from it efficiently such as metals (e.g. Copper, Aluminium) or ceramics (e.g. Alumina, Aluminium Nitride), composites (e.g. Carbon and Graphite fillers) and graphite (e.g. Pyrolytic Graphite). The inside of the measuring chamber should have a high surface to volume ratio to maximise heat conduction from the gas, thus a thin flat surface is advantageous. The volume/surface area ratio is preferably minimized to less than 40 centimeters, more preferably less than 35 cm. The heatsink block can be made of a single material or a combination of materials that have a high thermal conductivity and a high heat capacity (e.g. aluminium, carbon steel or copper). The heatsink containing the measuring chamber may be further mounted or attached to another heat sink element with a high heat capacity and thermal conductivity such as Aluminium or Copper to evacuate heat away from the measuring chamber thus ensuring that the temperature in the chamber returns rapidly to the ambient temperature after the heater switches off.

The common support structure 14 may advantageously act as the main heat sink plate for the sensor. The material and mass of the common support structure may be chosen such the specific heat capacity thereof is configured so that the temperature doesn't significantly increase, for instance less than 0.5° C., during a measurement.

The resistive passage 18 may in particular and in a preferred embodiment be in the form of a capillary channel, namely a long small diameter channel configured to provide a fluidic resistance that restricts the flow into and out of the measuring chamber 16 with an exponential time constant that allows sufficiently accurate measurement of the variation of pressure in the measuring chamber as gas flows into and out of the measuring chamber due to a difference in pressure between the pressure in the measuring chamber and pressure in the gas receiving chamber 38. The concept of capillary channel in a gas viscosity sensor is per se well known and the dimensions and characteristics of this do not need to be further disclosed. The capillary is any structure that causes fluidic resistance to gas flowing through such as narrow straight or meandering tube or a channel in a block of material (e.g. silicon, metal, plastic or ceramic). There may also be more than one capillary channel forming a resistive passage. Within the scope of the invention, gas flow resistive passages of other types may however also be used, for instance a passage obstructed with a filter element, gas permeable membrane or simply a wall with a small orifice.

The pressure sensor 28 is configured to measure the pressure in the measuring chamber and in particular to measure the variation of pressure in the measuring chamber which varies according to the operation of the pressure generator 25.

According to an aspect of the invention, the gas viscosity sensor 4 further comprises a reference chamber system 21 that comprises a reference chamber 22 fluidically connected to the gas interface portion 20, more specifically the gas receiving chamber 38, via a second resistive passage 24, the reference chamber 22 being coupled to the pressure sensor 28 via an interface portion 32. In the foregoing configuration, the pressure sensor 28 is configured to measure a differential pressure between the measuring chamber 16 and the reference chamber 22. This advantageously allows to adjust for pressure variations in the gas receiving chamber 38, in particular to cancel the effects of variations of pressure in the gas receiving chamber on the viscosity measurement. In this regard, the resistive passage 24 may have a similar or identical configuration to the first resistive passage 18 in order to have a similar resistive behavior on gas flowing in and out of the reference chamber to that of the gas flowing in and out of the measuring chamber.

The size of reference chamber 22 and the second resistive passage 24 are chosen such that the time constant of the reference chamber is preferably not less than 10% of the time constant of the measuring chamber.

In an advantageous embodiment, the pressure sensor 28 may comprise a membrane sensor comprising a flexible membrane forming an interface between the measuring chamber 16 and the reference chamber 22 such that the membrane is directly affected by the differential pressure between the measuring and reference chambers. The similar or identical resistive passages 18 and 24 ensure that pressure fluctuations in the gas receiving chamber 38 have a similar or identical time varying effect (having a similar time constant) on the pressure at the measuring chamber end, respectively reference chamber end, of the resistive passage 18, 24. The second resistive passage and reference chamber thus dampen rapid changes in pressure at the end of the first resistive passage connected to the measuring chamber. This reduces noise in the differential pressure measurement and protects the differential pressure transducer from pressure shocks (rapid changes in external pressure to extreme high or low values).

The reference chamber system may advantageously further comprise a heat evacuator 34 for instance in form of a passive heat sink, comprising for instance a sufficiently large mass of thermally conductive material such that the temperature of the reference chamber heat sink is essentially the same or very close to that of the measuring chamber heat sink 30 in order to diminish the effects of temperature variations on the differential pressure measurement.

In an embodiment, the measuring chamber 16 and reference chamber 22 may advantageously be arranged on opposite sides of a circuit board 10, whereby the heat evacuator 34 in the form of a heat sink of the reference chamber system 22 is positioned on an opposite side of the circuit board from the heat evacuator 30 in the form of a heat sink of the measuring chamber system 15. The heat evacuators may be formed of blocks of metal, preferably copper or aluminium or alloys thereof, which may be bonded to the surface of the circuit board or welded or soldered thereto.

The pressure sensor 28 of the measuring chamber system 15 may advantageously be positioned within the reference chamber 22 of the reference chamber system 21, communicating with the measuring chamber 16 through an orifice 53 in the circuit board 10.

The pressure sensor 28 may advantageously be mounted on a dedicated circuit board 54 that forms also a portion of the housing of the measuring chamber 16 the measuring chamber housing being completed by a cap portion 56 mounted on the independent circuit board 54. The independent circuit board may be provided with circuit traces and further electronic components as needed, the circuit traces having contact pads for connection to the circuit board 10 of the signal processing circuit 8.

Figure 9A:
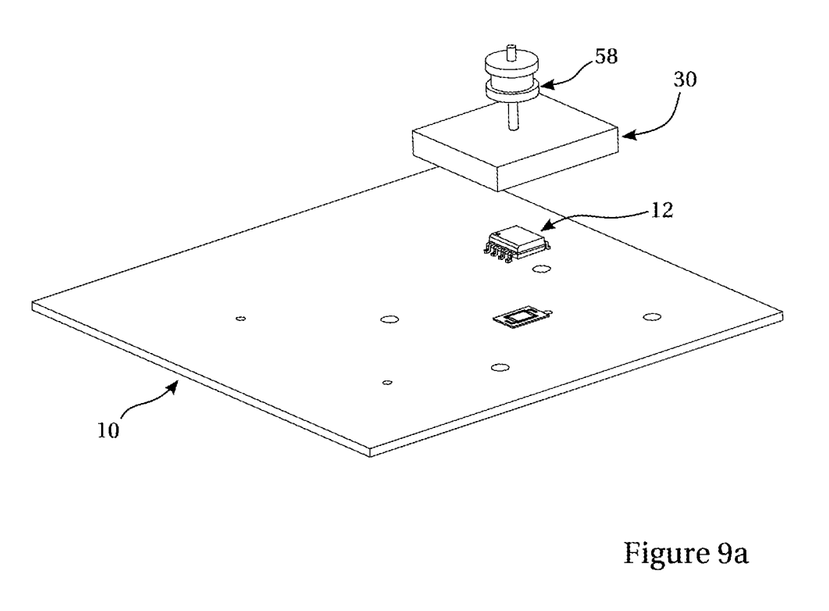
FIGS. 9a, 9b are perspective views of a gas sensor according to an embodiment of this invention during assembly.
Figure 9B:
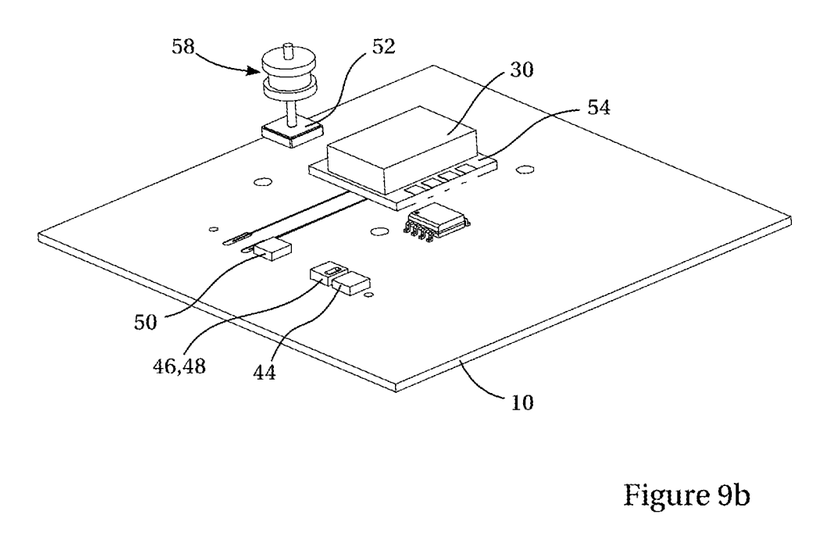
Figure 10:
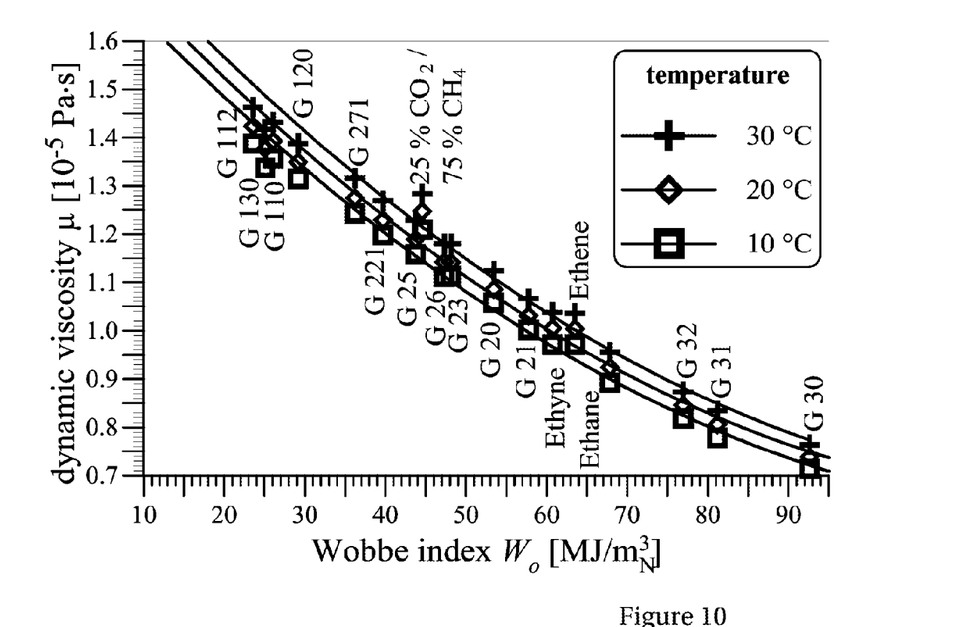
FIG. 10 is a graph representing a known relationship between dynamic viscosity and the Wobbe index of different combustible gases at different temperatures.

Various components such as the measuring chamber system 15, the heat evacuator 34 of the reference chamber system, the micro-controller 12, the housing 36 of the gas receiving chamber 38 may positioned on the circuit board 10 by a pick and place tool 58 of an automated assembly machine thus reducing assembly costs. The auxiliary sensors 6 may also be positioned on the circuit board by means of the pick and place tool.

Figure 4A:
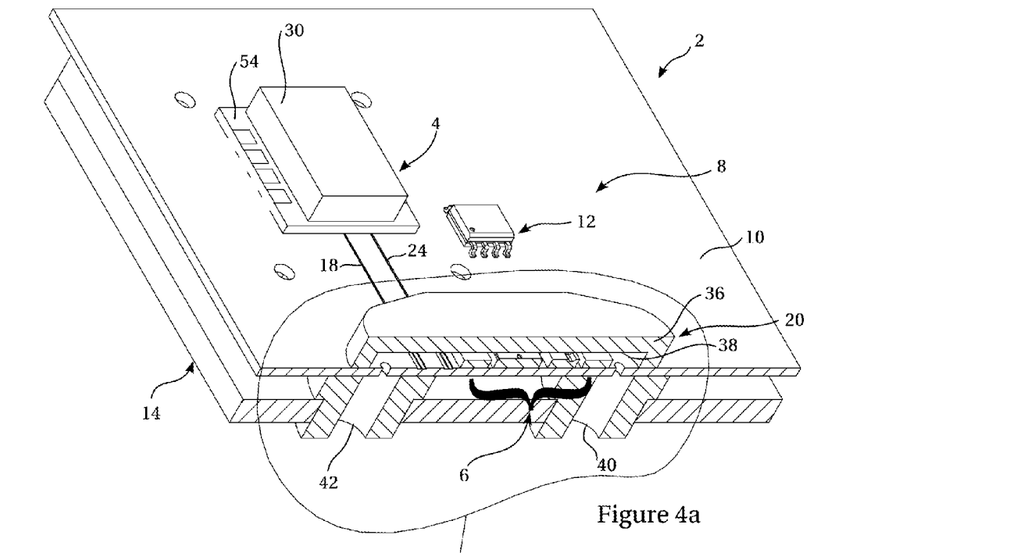
Figure 4B:
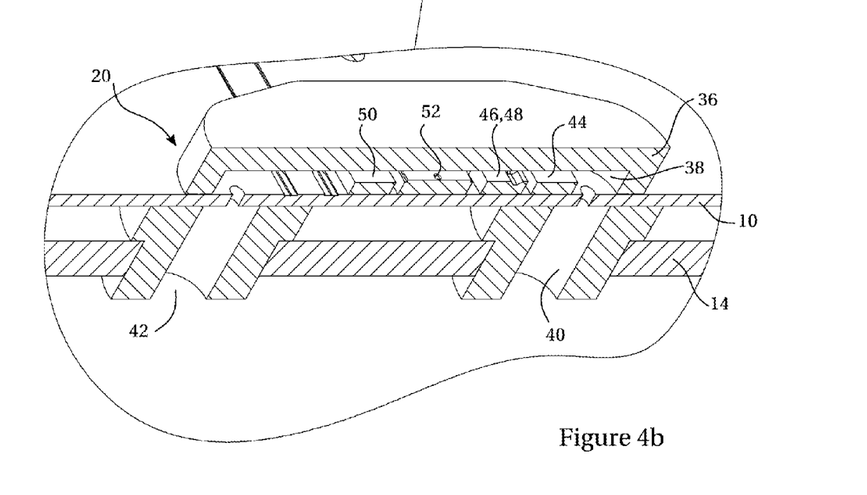
Figure 5:
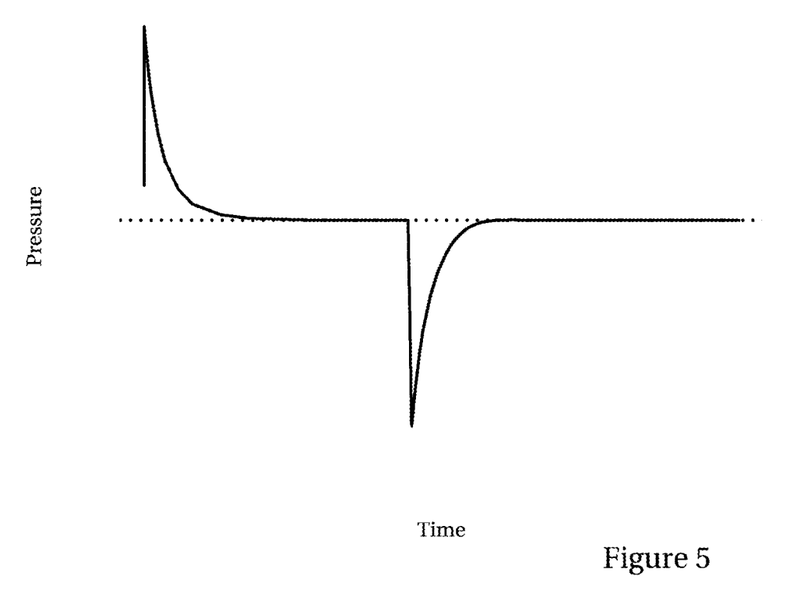
FIG. 5 is a graphical representation of a pressure vs time behavior in a measuring chamber of a gas sensor according to an embodiment of the invention.
Figure 6:
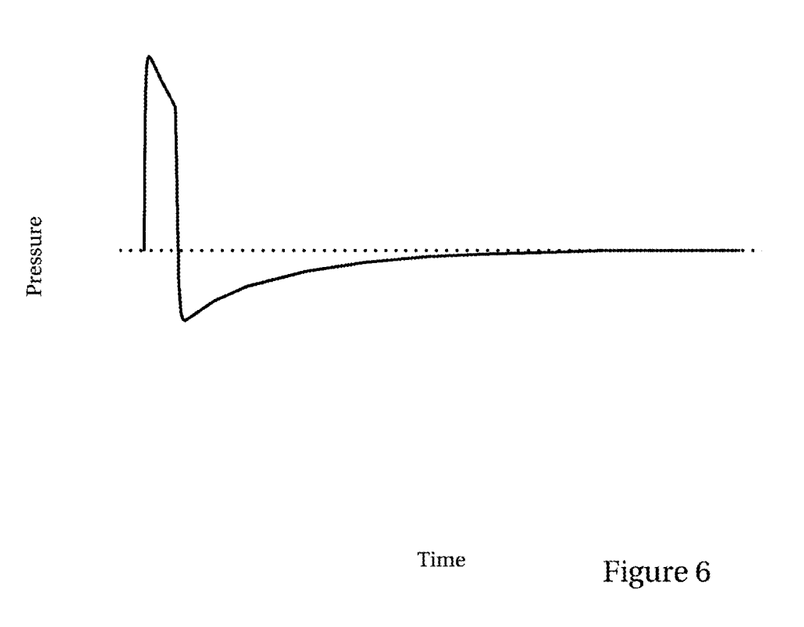
FIG. 6 is a graphical representation of a pressure vs time behavior in a measuring chamber of a gas sensor according to an embodiment of the invention.

The support structure 14 as illustrated in FIG. 4a may form part of a housing (not shown) of the gas sensor 2, that is adapted to be positioned in an environment in which gas 1 to be measured flows or to be connected via the inlets and outlets to a conduit or container in which the gas 1 to be measured flows or is contained.

The absolute pressure sensor 52 may be used to correct for variations in the gas flow through the capillary due to the level of absolute pressure of the sample gas.

The temperature sensor 48 may be used to compensate for variations in the gas flow through the resistive passage 18 due to changes in temperature.

The humidity sensor 46 may be used to compensate for variation in the gas flow through the resistive passage 18 due to changes in the moisture content in the gas 1 to be measured.

Depending on the accuracy required, the addition of a thermal conductivity sensor 50 can be used to improve the accuracy of the Wobbe index measurement by measuring the thermal conductivity of the gas at two temperatures.

Figure 7:
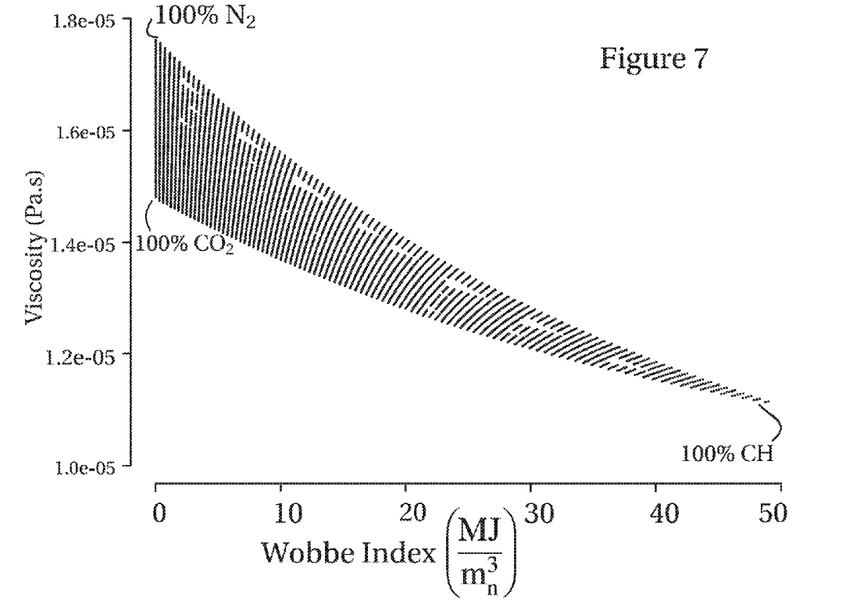
FIG. 7 is a graphical representation of Viscosity vs Wobbe Index values for the different gases N2, CO2, and CH4.

A $CO_2$ sensor 44 can also be used to improve the accuracy of Wobbe index measurement. FIG. 7 shows the relationship between mixtures of $N_2$, $CO_2$ and $CH_4$, with 100% mixtures of each of the gases labelled. It can be seen that $CO_2$ has a lower viscosity than $N_2$ and thus would introduce more error into the measurement as the viscosity is closer to that of $CH_4$. It is thus advantageous to measure the concentration of $CO_2$ to reduce the error in the conversion from the viscosity of the gas to its Wobbe index.

The signal processing circuit 8 may comprise a memory unit for storing time based data from the sensors. The data can then be processed to determine the viscosity from the profile of the differential pressure data which is compensated using data from the absolute pressure, temperature and humidity transducers, and comparing it to stored calibrations values. In addition the circuit may have the facility to turn the heater on and off and control the temperature of the heater when it is switched on. Further to this the signal processing unit may store a look-up table or formula to convert the viscosity measurement to a Wobbe index value. Using data from the thermal conductivity sensor, the accuracy of the Wobbe index measurement can be improved and the higher heating value (HHV) can be determined. Alternatively or in conjunction with the thermal conductivity transducer a $CO_2$ transducer can also be used to improve the accuracy of the Wobbe index measurement. After the Wobbe index and HHV are calculated the signal processing circuit may communicate the data to another device or human operator.

The differential pressure sensor 28 may comprise a flexible membrane 55, for instance a silicon membrane, with piezo-resistive elements to measure the deformation of the membrane representing the pressure difference between the inside and the outside of the measuring chamber. The pressure on the outer side of the membrane should be essentially equal, absent the noise fluctuations, to the pressure at the gas receiving side of the resistive passage 18.

The transducers for absolute pressure, temperature, humidity, thermal conductivity and CO2 may be implemented as separate silicon dies or surface mount components and can communicate their output to the signal processing circuits using analogue or digital signals. The signal processing circuit may comprise a digital microcontroller 12 that can read the analogue and digital output from the transducers, and further store the data to memory and perform analysis of the differential pressure measurement, the absolute pressure data, the humidity data and the temperature data to determine the gas viscosity. A look up table stored in memory or a mathematical formula can then be used to calculated the Wobbe index and higher heating value using the thermal conductivity measurements and $CO_2$ measurement.

To measure the viscosity, Wobbe index and higher heating value the signal processing circuit can for instance operate with either of two modes of operation:

1. The heater 26 is switched on and supplies heat to the gas and the temperature of the gas is kept constant. This creates an initial rapid rise in the pressure difference between the measuring chamber and the gas receiving end of the capillary. As the temperature of the gas in the measuring chamber remains constant the gas flows through the capillary causing the pressure difference to drop in an exponential decay from which the time constant is measured. When the pressure difference returns to zero the heat is switched off completely causing a rapid decrease in gas temperature as the heat is transmitted through the walls of the measuring chamber to the heat sink 30. This causes a rapid decrease in pressure between the measuring chamber and the end of the capillary causing gas to flow back through the capillary. As the gas flows back the pressure increases as an inverse exponential decay to zero from which the time constant is measured. The sensor can measure continuously by turning on the heater again and repeating the method allowing two time constant measurements—one as the gas leaves the measuring chamber and a second when the measuring chamber draws the gas in.
2. The second mode is where the gas in the measuring chamber is heated as above but it is not necessary to control the temperature. The maximum temperature is limited for safety reasons (to prevent combustion or charring). This causes a rapid increase in pressure and subsequent gas flow out of the cavity through the capillary. The flow of the gas is allowed to continue for short period of time and then the heater is switched off. The heat in the gas is transmitted rapidly through the walls of measuring chamber to the heat sink causing a negative pressure difference between the measuring chamber and capillary end. As the gas flows back through the capillary the pressure difference returns to zero as an inverse exponential decay. The time constant of this exponential decay is measured.

For both modes the viscosity $\eta$ is calculated as $\eta = \alpha \times \tau \times P_0$, where $\alpha$ is defined as the sensor constants—the dimensions of the capillary and the measuring chamber, $\tau$ is the time constant of the differential pressure measurement and $P_0$ is the absolute pressure of the gas outside the sensor. The temperature data is used to compensate for variations in the value of a which changes with respect to temperature.

The sensor can be assembled onto a single or multiple planar substrates such as printed circuit board 10, hybrid thick film or Low Temperature Cofired Ceramic. This would allow the viscometer, capillaries, differential pressure transducer, heater and measuring chamber to be assembled with the electronics necessary to construct the signal processing circuit and additional transducers (Absolute Pressure, Temperature, Humidity, Thermal Conductivity and $CO_2$ transducers). These components can be assembled on the substrate as either soldered surface mount components or as silicon dies to form a Multi Chip Module (MCM). The planar construction of the sensor enables the possibility for the sensor to be assembled using automated methods such as a robotic pick and place machines commonly used for assembling electronics. This allows to manufacture the sensor at low cost.

Figure 11A:
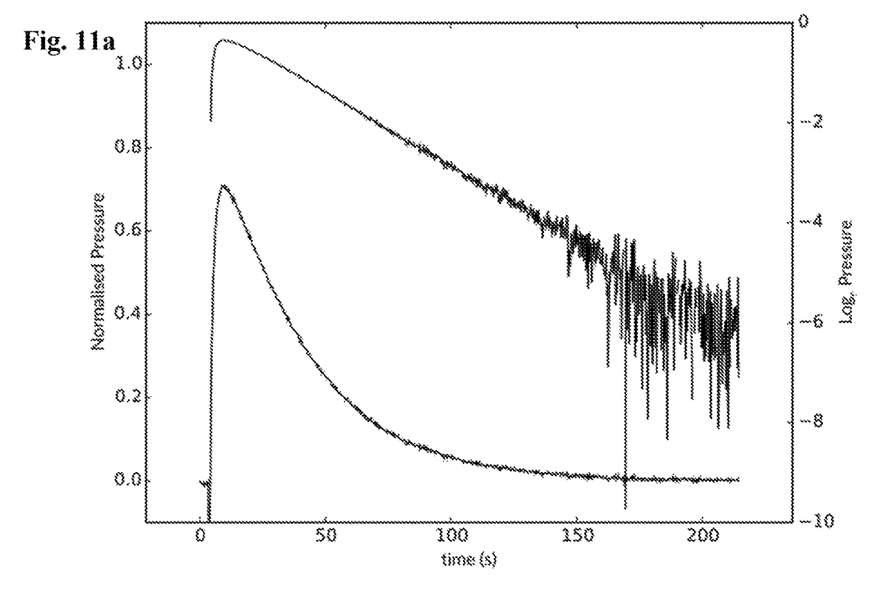
FIG. 11a is a graph showing test results of measured pressure over time of an experimental setup blowing air with a fan and using a gas sensor without reference chamber and capillary (i.e. according to the prior art)
Figure 11B:
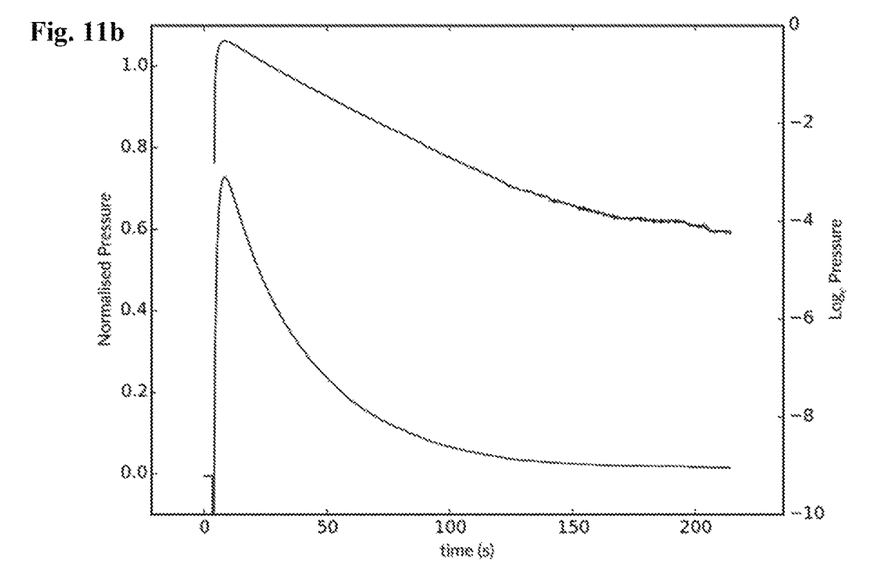
FIG. 11b is a graph showing test results of measured pressure over time of an experimental setup blowing air with a fan and using a gas sensor with reference chamber and capillary according to an embodiment of the invention.

Referring to FIGS. 11a and 11b, a sensor was placed in a chamber to measure the viscosity of air. To create turbulence (i.e. randomly fluctuating air pressure) an fan was used. The sensor was equipped with only one capilliary connected to the measuring chamber 16 and the reference chamber 26 was left open to the turbulent air in a configuration comparable to that of the gas sensor described in (US2009/0229351 A1).

The output of the differential pressure measurement is shown by the curve in the bottom of FIG. 11a and its natural logarithm plotted above. The noise generated by the turbulent air is clearly visible in both plots.

A second sensor was assembled with a reference chamber 26 and capillary 24 according to an embodiment of the invention and tested under identical conditions to the above experiment. The test results are plotted in FIG. 11b and show an improvement in the smoothness of the pressure measurement without altering the transient signal. This can be seen in both the plot of the differential pressure and it natural log plotted above.

LIST OF REFERENCES

Gas 1
Gas sensor 2
  Gas viscosity sensor 4
    Gas interface portion 20
      Housing 36
        Gas receiving Chamber 38
      Inlet 40
      Outlet 42
    Measuring chamber system 15
      Measuring chamber 16
      Pressure generator 25
        Heater 26
        Heat evacuator 30
        heat sink
      Pressure sensor 28
        Dedicated circuit board 54
        Membrane 55
      (First) Resistive passage 18
        capillary
    Reference chamber system 21
      Reference chamber 22
      Interface portion 32
      Heat evacuator 34
        Heat sink
      (second) Resistive passage 24
        capillary
  Auxiliary sensors 6
    CO2 sensor 44
    Humidity sensor 46
    Temperature sensor 48
    Thermal conductivity sensor 50
    Absolute pressure sensor 52
  Signal processing circuit 8
    Circuit board 10
      Orifice 53
      Microcontroller 12
  Support structure 14
  Pick and place tool 58

The invention claimed is:

1. Gas sensor for measuring properties of a gas, including a gas viscosity sensor comprising a gas interface portion in contact with the gas to be measured, and a measuring chamber system comprising a measuring chamber, a first resistive passage fluidically connecting the measuring chamber to the gas interface portion, a pressure generator configured to generate a change in pressure in the measuring chamber, and a pressure sensor configured to measure a time dependent variation in pressure of gas in the measuring chamber, the time dependent variation of pressure in the measuring chamber due to flow of gas through the resistive passage being correlated to a viscosity of the gas, wherein the gas viscosity sensor further comprises a reference chamber system comprising a reference chamber and a second resistive passage fluidically interconnecting the reference chamber to the gas interface portion, the reference chamber being coupled to the pressure sensor of the measuring chamber such that the pressure sensor is configured to measure a differential pressure between a pressure in the measuring chamber and a pressure in the reference chamber, wherein the first resistive passage and second resistive passage are in the form of capillary channels.

2. Gas sensor according to claim 1, wherein the pressure sensor comprises an elastically deformable membrane the displacement of which provides a measurement value of the differential pressure, the deformable membrane forming an interface between a volume of gas contained in the measuring chamber and the volume of gas contained in the reference chamber.

3. Gas sensor according to claim 1, wherein the pressure generator of the measuring chamber system comprises a heater positioned in the measuring chamber and configured to heat the gas therein, and a heat evacuator to cool the gas in the measuring chamber.

4. Gas sensor according to claim 3, wherein the heat evacuator is in the form of a heat sink formed of a mass of thermally conductive material with a heat capacity significantly larger than the heat capacity of the gas contained in the measuring chamber.

5. Gas sensor according to claim 4, wherein the heat sink is made of a block of metal with a thermal diffusivity greater than $8 \times 10^{-5}$ (m$^2$/s).

6. Gas sensor according to claim 1, further comprising a signal processing circuit comprising a circuit board.

7. Gas sensor according to claim 6, wherein the pressure generator comprises a heater, the heater comprising a resistive element formed as resistive circuit traces on the circuit board, or as a resistance element mounted directly on the circuit board.

8. Gas sensor according to claim 1, wherein the measuring chamber is formed in a cavity provided in a heat sink of the measuring chamber system.

9. Gas sensor according to claim 1, wherein the gas interface portion comprises a housing defining a gas receiving chamber connected via an inlet and outlet to a gas flow system through which the gas to be measured flows.

10. Gas sensor according to claim 1, further comprising one or more auxiliary sensors selected from a group comprising CO2 sensor, humidity sensor, temperature sensor, thermal conductivity sensor, absolute pressure sensor.

11. Gas sensor according to claim 10, wherein the auxiliary sensor includes at least a $CO_2$ sensor.

12. Gas sensor according to claim 10, wherein a plurality of sensors are provided and at least some of the auxiliary sensors are positioned in a gas receiving chamber of the gas interface portion.

13. Gas sensor for measuring properties of a gas, including a gas viscosity sensor comprising a gas interface portion in contact with the gas to be measured, and a measuring chamber system comprising a measuring chamber, a first resistive passage fluidically connecting the measuring chamber to the gas interface portion, a pressure generator configured to generate a change in pressure in the measuring chamber, and a pressure sensor configured to measure a time dependent variation in pressure of gas in the measuring chamber, the time dependent variation of pressure in the measuring chamber due to flow of gas through the resistive passage being correlated to a viscosity of the gas, wherein the gas viscosity sensor further comprises a reference chamber system comprising a reference chamber and a second resistive passage fluidically interconnecting the reference chamber to the gas interface portion, the reference chamber being coupled to the pressure sensor of the measuring chamber such that the pressure sensor is configured to measure a differential pressure between a pressure in the measuring chamber and a pressure in the reference chamber wherein the reference chamber is arranged on an opposite side of a circuit board to the measuring chamber.

14. Gas sensor according to claim 13, wherein the pressure sensor is mounted within the reference chamber and fluidically connected via an orifice in the circuit board to the measuring chamber.

15. Gas sensor according to claim 13, wherein the pressure generator comprises a heater, the heater comprising a resistive element formed as resistive circuit traces on the circuit board, or as a resistance element mounted directly on the circuit board.

16. Gas sensor according to claim 13, wherein the pressure sensor comprises an elastically deformable membrane the displacement of which provides a measurement value of the differential pressure, the deformable membrane forming an interface between a volume of gas contained in the measuring chamber and the volume of gas contained in the reference chamber.

17. Gas sensor according to claim 13, wherein the pressure generator of the measuring chamber system comprises a heater positioned in the measuring chamber and configured to heat the gas therein, and a heat evacuator to cool the gas in the measuring chamber.

18. Gas sensor according to claim 17, wherein the heat evacuator is in the form of a heat sink formed of a mass of thermally conductive material with a heat capacity significantly larger than the heat capacity of the gas contained in the measuring chamber.

19. Gas sensor according to claim 18, wherein the heat sink is made of a block of metal with a thermal diffusivity greater than $8 \times 10-5$ (m2/s).

20. Gas sensor according to claim 13, wherein the measuring chamber is formed in a cavity provided in a heat sink of the measuring chamber system.

21. Gas sensor according to claim 13, wherein the gas interface portion comprises a housing defining a gas receiving chamber connected via an inlet and outlet to a gas flow system through which the gas to be measured flows.

22. Gas sensor according to claim 13, further comprising one or more auxiliary sensors selected from a group comprising $CO_2$ sensor, humidity sensor, temperature sensor, thermal conductivity sensor, absolute pressure sensor.

23. Gas sensor according to claim 22, wherein at least some of the auxiliary sensors are positioned in a gas receiving chamber of the gas interface portion.

* * * * *